United States Patent
Donofrio

(10) Patent No.: US 8,512,254 B2
(45) Date of Patent: Aug. 20, 2013

(54) OPTICAL SENSOR AND METHOD FOR DETECTING A PATIENT CONDITION

(75) Inventor: William T. Donofrio, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/566,057

(22) Filed: Aug. 3, 2012

(65) Prior Publication Data

US 2012/0303081 A1   Nov. 29, 2012

Related U.S. Application Data

(63) Continuation of application No. 11/963,045, filed on Dec. 21, 2007, now Pat. No. 8,260,415.

(51) Int. Cl.
  *A61B 5/02*   (2006.01)
(52) U.S. Cl.
  USPC .............................................. 600/507; 607/6
(58) Field of Classification Search
  USPC ............ 607/3, 6, 17–22; 600/301, 322–324, 600/333, 500, 507–508
  See application file for complete search history.

(56) References Cited

U.S. PATENT DOCUMENTS

| | | | |
|---|---|---|---|
| 5,033,472 A | 7/1991 | Sato et al. | |
| 6,122,536 A | 9/2000 | Sun et al. | |
| 6,125,290 A | 9/2000 | Miesel | |
| 6,491,639 B1 * | 12/2002 | Turcott | 600/508 |
| 6,575,912 B1 | 6/2003 | Turcott | |
| 6,997,879 B1 * | 2/2006 | Turcott | 600/507 |
| 7,177,686 B1 | 2/2007 | Turcott | |
| 2002/0026108 A1 | 2/2002 | Colvin | |
| 2004/0039269 A1 | 2/2004 | Ward et al. | |
| 2004/0176669 A1 | 9/2004 | Colvin | |
| 2004/0220629 A1 | 11/2004 | Kamath et al. | |
| 2007/0015981 A1 | 1/2007 | Benaron et al. | |
| 2007/0156085 A1 | 7/2007 | Schulhauser et al. | |
| 2007/0239215 A1 * | 10/2007 | Bhunia et al. | 607/6 |
| 2007/0255148 A1 | 11/2007 | Bhunia | |
| 2008/0208020 A1 | 8/2008 | Cinbis et al. | |

FOREIGN PATENT DOCUMENTS

| | | | |
|---|---|---|---|
| WO | 2004091719 A2 | 10/2004 | |
| WO | WO 2004091719 A2 * | 10/2004 | |
| WO | 2006113394 A2 | 10/2006 | |

* cited by examiner

*Primary Examiner* — Rex R Holmes
(74) *Attorney, Agent, or Firm* — Evans M. Mburu

(57) ABSTRACT

An implantable medical device for monitoring tissue perfusion that includes a light source emitting a light signal and a light detector receiving emitted light scattered by a volume of body tissue. The light detector emits a signal having an alternating current component corresponding to the pulsatility of blood flow in the body tissue volume. A processor receives the current signal and determines a patient condition in response to the alternating component of the current signal.

9 Claims, 6 Drawing Sheets

OPTICAL SENSOR AND METHOD FOR DETECTING A PATIENT CONDITION

CROSS-REFERENCE TO RELATED APPLICATIONS

The present application claims priority from U.S. patent application Ser. No. 11/963,045 filed Dec. 21, 2007, now issued as U.S. Pat. No. 8,260,415, the entire disclosure of which is incorporated herein by reference.

FIELD

The invention relates generally to implantable medical devices and, in particular, to an implantable optical sensor for use in a medical device system for detecting a patient condition.

BACKGROUND

Implantable medical devices (IMDs) for monitoring a physiological condition or delivering a therapy typically include one or more physiological sensors. Physiological sensors used in conjunction with an IMD provide a signal related to a physiological condition from which a patient state or the need for a therapy can be assessed. Examples of such IMDs include heart monitors, pacemakers, implantable cardioverter defibrillators (ICDs), myostimulators, neurological stimulators, drug delivery devices, insulin pumps, glucose monitors, etc.

Optical sensors are employed in IMDs as physiological sensors configured to detect changes in light modulation by a body fluid or tissue measurement volume due to a change in a physiological condition in the body fluid or tissue. Such optical sensors can be used, for example, for detecting changes in metabolite levels in the blood, such as oxygen saturation levels or glucose level, or changes in tissue perfusion. Monitoring such physiological conditions provides useful diagnostic measures and can be used in managing therapies for treating a medical condition. For example, a decrease in blood oxygen saturation or in tissue perfusion may be associated with insufficient cardiac output or respiratory function. Thus monitoring such signals allows an implantable medical device to respond to a decrease in oxygen saturation or tissue perfusion, for example by delivering electrical stimulation therapies to the heart to restore a normal hemodynamic function.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

Figure 1:
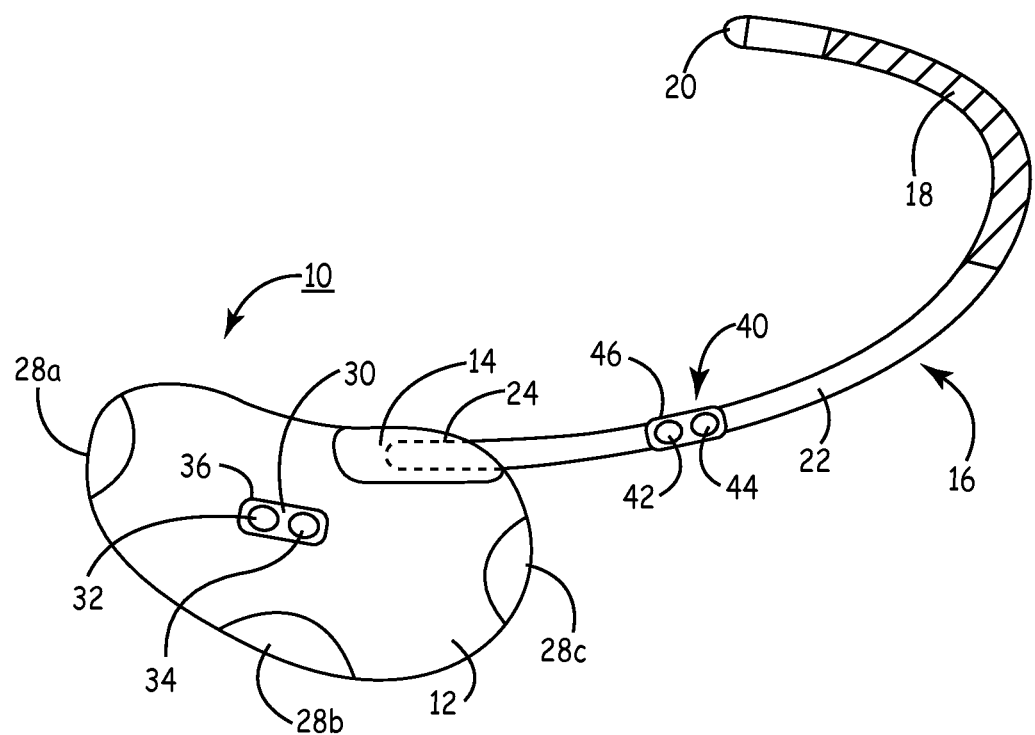
FIG. 1 is an illustration of one IMD configuration in which an optical sensor and associated method for determining a patient condition may be implemented.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is an illustration of one IMD configuration in which an optical sensor and associated method for determining a patient condition may be implemented. The IMD is shown embodied as a subcutaneous implantable cardioverter defibrillator (SubQ ICD) 10. SubQ ICD 10 includes a housing 12 with a connector 14 for attaching a subcutaneous sensing and cardioversion/defibrillation therapy delivery lead 16.

Subcutaneous lead 16 includes a distal defibrillation coil electrode 18, a distal sensing electrode 20, an insulated flexible lead body 22 and a proximal connector pin 24 for connection to SubQ ICD 10 via connector 14. SubQ ICD 10 further includes multiple electrodes 28a, 28b, and 28c, incorporated along housing 12 and referred to collectively as subcutaneous electrode array (SEA) 28. SEA 28 is shown welded into place on the periphery of the housing of SubQ ICD 10 and is connected via wires to electronic circuitry within housing 12. SEA 28 shown in FIG. 1 includes three electrodes 28a, 28b and 28c positioned to form orthogonal signal vectors though other embodiments may include any number of subcutaneous housing-based electrodes. Any of the electrodes included in SEA 28 or on subcutaneous lead 16 may be selected in any combination for sensing subcutaneous ECG signals for use in monitoring a patient's heart rhythm and synchronizing anti-arrhythmia therapies.

According to embodiments of the present invention, SubQ ICD 10 further includes an optical sensor 30, also referred to herein as a tissue perfusion sensor (TPS) 30, for detecting tissue perfusion. TPS 30 is assembled within housing 12 along a window 36 formed in housing 12. TPS 30 includes a light emitting portion 32 and a light detecting portion 34. As will be described in detail herein, light emitting portion 32 emits light through window 36. The emitted light is scattered by a tissue volume adjacent to or in contact with SubQ ICD 10 at the implant site. Light detecting portion 34 detects the scattered light incident on detecting portion 34 and generates a signal responsive to changes in the intensity of the incident light. The TPS signal is used by SubQ ICD 10 in detecting or confirming a patient condition, e.g. a cardiac arrhythmia, which in turn may trigger the delivery of a therapy, e.g. an anti-arrhythmia therapy such as a defibrillation shock, by SubQ ICD 10.

Additionally or alternatively, a TPS 40 may be carried by subcutaneous lead 16. TPS 40 is assembled within lead body 22 along a window 46 formed in the lead body 22. Control signals for causing a light source within light emitting portion 42 are generated by SubQ ICD 10 and transmitted to light emitting portion 42 along a conductor (not shown) carried by lead 16. Light is emitted through window 46 from light emitting portion 42. The emitted light is scattered by an adjacent tissue volume, and scattered light is detected by light detecting portion 44. A signal generated by light detecting portion 44 is transmitted SubQ ICD 10 along a conductor (not shown) carried by lead 16.

The signals generated by TPS 30 and 40 are responsive to physiological changes in the targeted tissue volume corresponding to the perfusion of the targeted tissue. In particular, the light signal detected by TPS 30 and TPS 40 includes a pulsatile or alternating current (AC) component due to the pulsatility of blood flow through the tissue. The pulsatility or AC component will decrease when tissue perfusion is compromised, for example due to a serious arrhythmia such as ventricular fibrillation. Accordingly, as used herein, "tissue perfusion sensor" refers to an optical sensor used for detecting physiological changes in a targeted tissue volume correlated to a change in the perfusion of the tissue volume.

Figure 2:
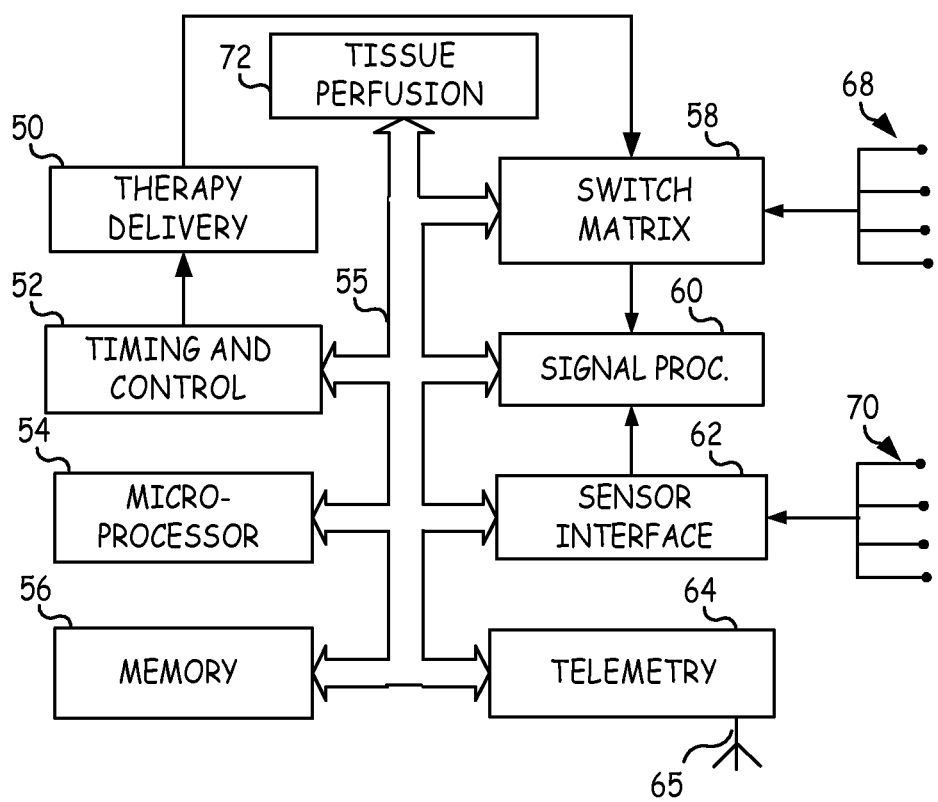
FIG. 2 is a functional block diagram of an ICD, such as the SubQ ICD shown in FIG. 1.

FIG. 2 is a functional block diagram of an ICD, such as SubQ ICD 10 shown in FIG. 1. SubQ ICD 10, referred to hereafter as "ICD 10", generally includes timing and control circuitry 52 and an operating system that may employ microprocessor 54 or a digital state machine for timing sensing and therapy delivery functions in accordance with a programmed operating mode. Microprocessor 54 and associated memory 56 are coupled to the various components of ICD 10 via a data/address bus 55. ICD 10 includes therapy delivery module 50 for delivering cardioversion/defibrillation shocks and optionally other cardiac pacing therapies or arrhythmia therapies, under the control of timing and control 52. Therapy delivery unit 50 is typically coupled to two or more electrode terminals 68 via a switch matrix 58. Switch matrix 58 is used for selecting which electrodes and corresponding polarities are used for delivering electrical stimulation pulses. Terminals 68 may be coupled to connectors providing electrical connection to SEA 28 and lead-based electrodes 18 and 20, shown in FIG. 1.

Electrode terminals 68 are also used for receiving cardiac electrical signals. Cardiac electrical signals are sensed for determining when an electrical stimulation therapy is needed and may be used in controlling a stimulation mode and the timing of electrical stimulation pulses, including CV/DF shocks. Electrodes used for sensing and electrodes used for stimulation may be selected via switch matrix 58. When used for sensing, electrode terminals 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias. Signal processing circuitry 60 may include event detection circuitry, e.g. R-wave detection circuitry, commonly used by implantable pacemakers and ICDs.

Arrhythmia detection algorithms may be implemented for detecting ventricular tachycardia (VT), ventricular fibrillation (VF) as well as atrial arrhythmias such as atrial fibrillation (A FIB). Ventricular event intervals (R-R intervals) sensed from the ECG signals are commonly used for detecting ventricular arrhythmias. In response to an arrhythmia detection, a programmed arrhythmia therapy is delivered by therapy deliver module 50 under the control of timing and control 52.

ICD 10 is additionally coupled to one or more physiological sensors via physiological sensor terminals 70. Physiological sensors may include pressure sensors, accelerometers, flow sensors, blood chemistry sensors, activity sensors or other physiological sensors known for use with implantable cardiac stimulation devices. Physiological sensors may be carried by leads extending from ICD 10 or incorporated in or on the ICD housing. In addition or alternatively to detecting an arrhythmia using cardiac electrical signals, other physiological signals may be relied upon for detecting and/or confirming the presence of an arrhythmia. In particular, sensor terminals 70 provide connection to a tissue perfusion sensor, which may be TPS 30 incorporated along the housing 12 of ICD 10 or TPS 40 carried by subcutaneous lead 16 as shown in FIG. 1.

Signals received at sensor terminals 70 are received by a sensor interface 62 which provides sensor signals to signal processing circuitry 60. Sensor signals are used by microprocessor 54 for detecting physiological events or conditions. In particular signals from a TPS 30 or 40 are received for determining changes in tissue perfusion, which can be an indication of insufficient cardiac output due to a cardiac arrhythmia or another hemodynamic or respiratory insufficiency. A tissue perfusion module 72 may be implemented for receiving TPS signals from sensor interface 62 or a signal processor 60. Tissue perfusion module 72 is configured to execute algorithms for determining a relative change or level of tissue perfusion using the TPS sensor and provides microprocessor 54 with tissue perfusion information. The tissue perfusion data may be used for determining the need for delivering a therapy under control of the operating system.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. A tissue perfusion monitoring algorithm may be stored in memory 56 and executed by microprocessor 54 with input received from electrode terminals 68 and/or sensor terminals 70 for detecting a change in tissue perfusion. Alternatively, tissue perfusion monitor 72 may be embodied as dedicated circuitry for receiving TPS signals for generating a signal indicating a change or relative level of tissue perfusion. As will be described below, timing and control 52 may respond to the tissue perfusion data by altering a pacing mode, pacing parameter, arrhythmia detection parameter, and/or arrhythmia therapy according to perfusion response data stored in memory 56. Data relating to tissue perfusion may be stored in memory 56 for later retrieval.

ICD 10 further includes telemetry circuitry 64 and antenna 65. Programming commands or data are transmitted during uplink or downlink telemetry between ICD telemetry circuitry 64 and external telemetry circuitry included in a programmer or monitoring unit. Telemetry circuitry 64 and antenna 65 may correspond to telemetry systems known in the art.

While FIGS. 1 and 2 refer generally to a subcutaneous ICD system, it is recognized that embodiments of the invention may be implemented in ICD systems including transvenous, intracardiac leads, epicardial leads or other lead systems as well as pacemakers, implantable neurostimulators, drug pumps, hemodynamic monitors, cardiac rhythm monitors, or any other implantable medical device monitoring a physiological condition of a patient.

Figure 3A:
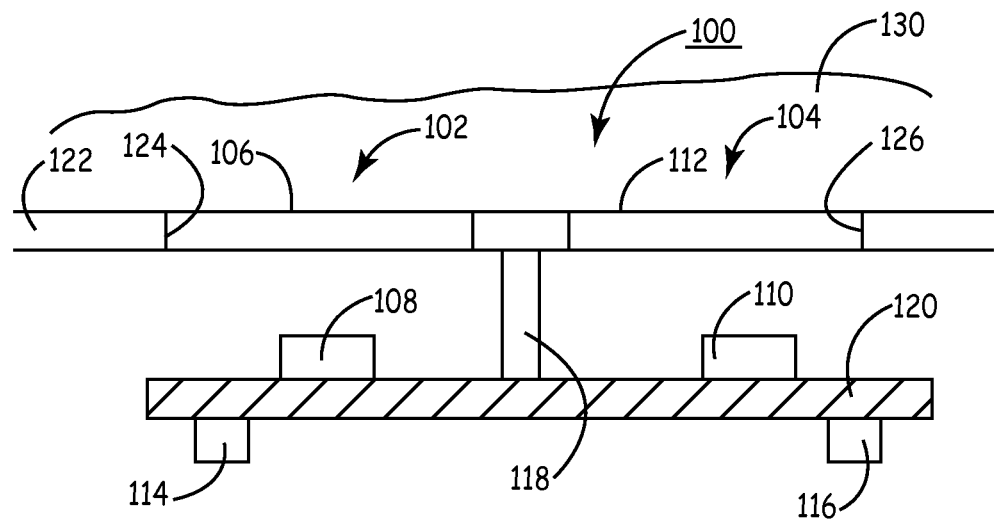
FIG. 3A is a schematic diagram of a TPS according to one embodiment of the present invention.

FIG. 3A is a schematic diagram of a TPS according to one embodiment of the present invention. TPS 100 shown in FIG. 3A and other TPS configurations described herein may be implemented in an implantable medical lead or in the housing of an implantable electronic device, such as subcutaneous ICD 10 or any other implantable pacemaker, ICD, neurostimulator, monitoring device, drug pump, or the like. TPS 100 includes a light emitting portion 102 and a light detecting portion 104. Light emitting portion 102 includes a light source 108 mounted on a circuit board 120 which enables electrical coupling to integrated circuitry 114 for delivering driver signals to light source 108. Light emitted by light source 108 in response to driver signals provided by integrated circuitry 114 passes through lens 106 mounted within a window 124 formed in housing 122. Housing 122 corresponds to an outer housing, capsule, or insulation of a device in which TPS 100 is implemented, such as SubQ ICD housing 12 or lead body 22 shown in FIG. 1. In some embodiments, a ferrule (not shown) may be used for mounting lens 106 in housing 122. Reference is made, for example, to U.S. Pat. No. 5,902,326 (Lessar, et al.), hereby incorporated herein by reference in its entirety.

Light detecting portion 104 includes a light detecting component 110 mounted on circuit board 120 and electrically coupled to integrated circuitry 116 which receives the current emitted by light detecting component 110 in response to scattered light incident on detecting component 110. Integrated circuitry 116 provides the light detecting component signal to processing circuitry, such as microprocessor 54 or tissue perfusion monitor 72 shown in FIG. 2. The processing circuitry is configured to perform an algorithm for detecting a change in a tissue perfusion using the received signal. Integrated circuitry 116 may include an analog-to-digital converter and flash memory for digitizing the analog signal and providing the digitized signal to processing circuitry.

Circuit board 120 is shown as a single circuit board on which both emitting portion 102 and detecting portion 104 are assembled. In alternative embodiments, separate circuit boards may be provided for each emitting and detecting portion. Emitting portion 102 and detecting portion 130 are separated by a light barrier 118 to prevent light emitted from light source 108 from being received directly by light detecting component 110. Light emitted from emitting portion 102 is scattered by an adjacent tissue volume 130. Scattered light passes through lens 112 mounted in window 126 of housing 122. Lenses 106 and 112 are commonly formed from sapphire.

Light source 108 is embodied as any opto-electronic component capable of emitting light in response to an applied current or voltage. Light source 108 may be embodied as an LED emitting a targeted wavelength such as visible red light. Light source 108 may emit light corresponding to other wavelengths in some embodiments. For example, light source 108 may be embodied as a white light source which emits a broad spectrum of light wavelengths.

Light detecting component 110, also referred to herein as a "light detector", is embodied as any opto-electronic component capable of emitting a current or voltage signal in the presence of light. Examples of light detecting components include photodetectors, photoresistors or light dependent resistors, photodiodes, phototransistors, photovoltaic cells, or charge-coupled devices. In one embodiment light detecting component 110 is embodied as a photodetector, such as a photo Darlington, and light source 108 is embodied as a red light LED. Red light emitted by source 108 and scattered by tissue volume 130 is detected by light detecting component 110. A signal generated by TPS 100 will include an AC component due to the pulsatility of the light signal caused by the pulsatility of blood flow through the tissue volume 130. TPS 100 is configured to detect a light wavelength, for example visible red light, that is expected to be highly responsive to the pulsatility of blood flow through the tissue.

Figure 3B:
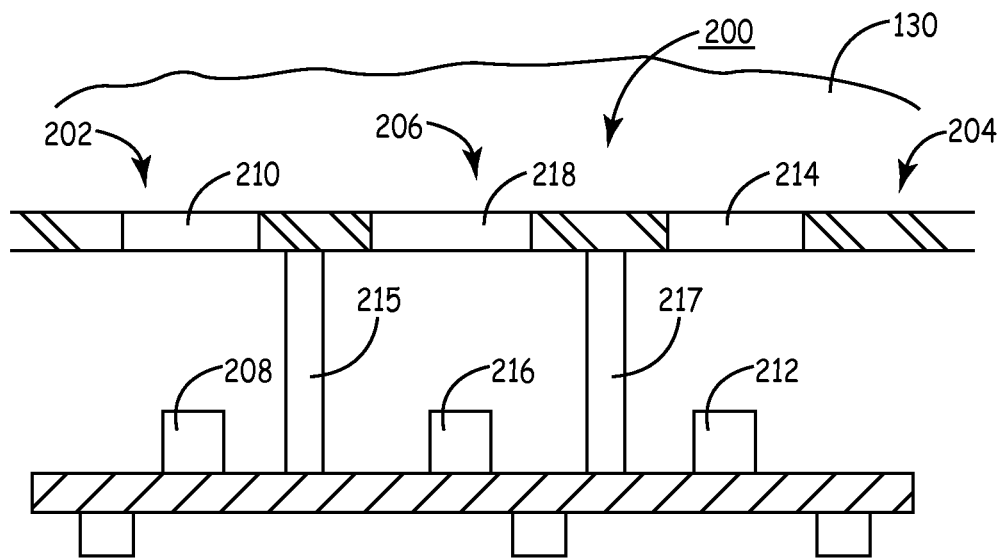
FIG. 3B is a diagram of a TPS including multiple light detecting portions.

FIG. 3B is a diagram of a TPS 200 including multiple light detecting portions 202 and 204 each including a light detecting component 208 and 212 receiving light through lenses 210 and 214, respectively. Light emitting portion 206 includes a light source 216 capable of emitting a desired light wavelength responsive to pulsatility of the blood flow in tissue volume 130. Light is emitted through lens 218 and scattered by tissue volume 130 back to the two light detection portions 202 and 204. Barriers 215 and 217 block light from traveling directly from emitting portion 206 to detecting portions 202 and 204. A second light detection signal from a second light detecting portion 204 receiving light from a second tissue site can be added to the first light detection signal from light detecting portion 202 to improve the received signal level or otherwise used to verify if pulsatility exists as an indicator of tissue perfusion.

Figure 4:
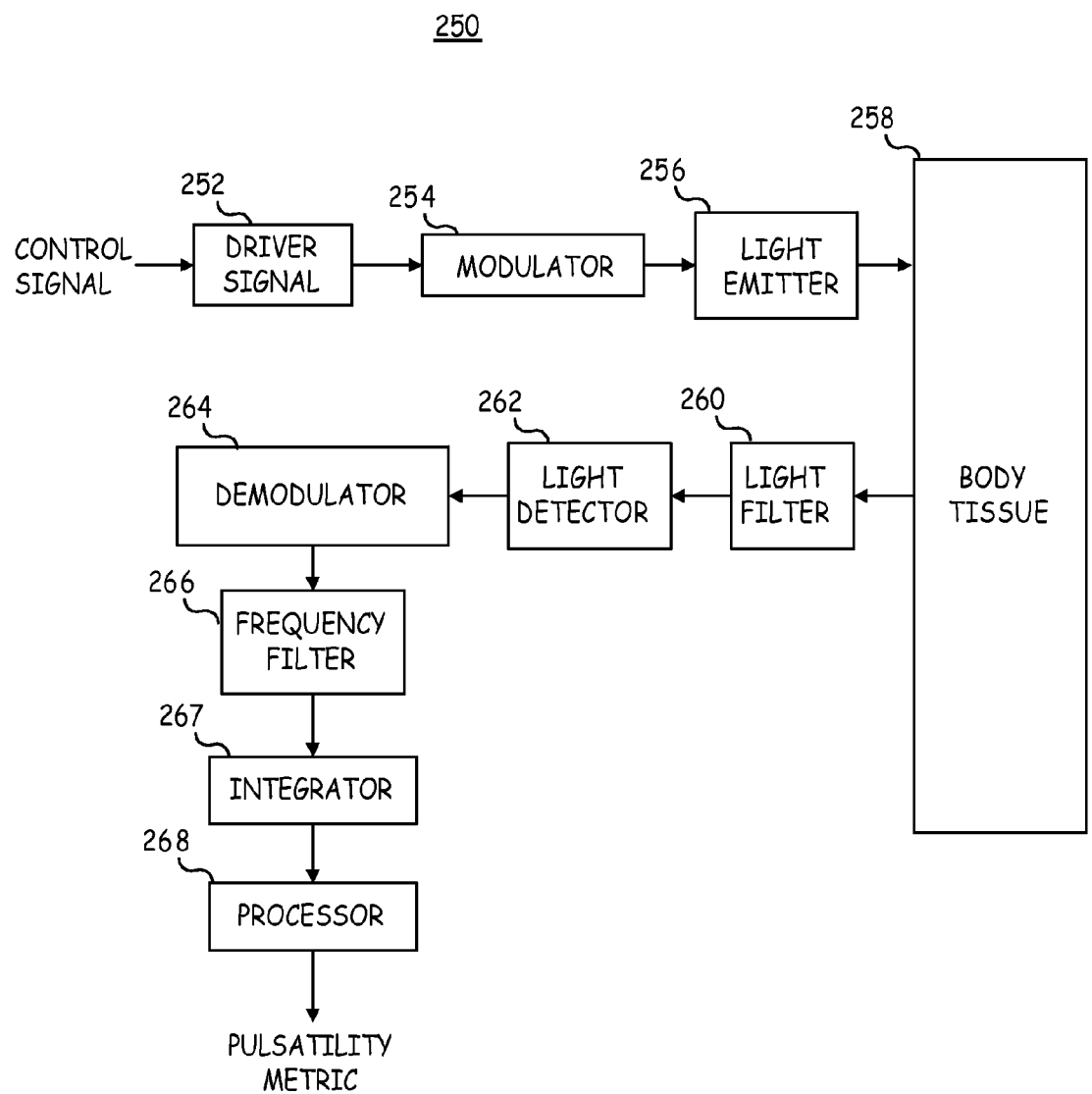
FIG. 4 is a functional block diagram of a TPS according to one embodiment of the invention.

FIG. 4 is a functional block diagram of a TPS 250 according to one embodiment of the invention. Driver signal circuitry 252 receives a control signal input from a timing and control module of an ICD or other associated implantable medical device. The driver signal output is modulated by modulator 254, which may be implemented in integrated circuitry 114 located on the same circuit board as a light source 108 as shown in FIG. 3A. Modulator 254 modulates the driver signal, for example a sine or square wave signal, using a high frequency carrier frequency, for example a 100 to 10,000 Hz carrier frequency.

The modulated driver signal is provided as input to light emitter 256 and causes light emitter 256 to emit a modulated light signal which is scattered by an adjacent volume of body tissue 258. The scattered light is optionally filtered by a light filter 260 to pass a selected light wavelength(s) to light detector 262. Light detector 262 generates a signal correlated to the intensity of the received scattered light. The detector signal is demodulated by demodulator 264, which may be included in integrated circuitry 116 on the same circuit board as the light detector as shown in FIG. 3B.

The demodulated light detector signal may be filtered by a frequency filter 266 to pass a narrow band of signal frequency corresponding to an expected heart rate range. For example, frequency filter 266 may be a narrow band pass filter passing signal frequencies corresponding to a heart rate range of 50 to 200 beats per minute.

It is recognized that in addition to demodulation and frequency filtering, the detector signal may be amplified by an amplifier (not shown) included in TPS 250. Modulation of the emitted light signal and demodulation of the detector signal reduces the effect of light noise, such as ambient light noise, that may be present in the detector signal.

The detector signal may be analyzed using an amplitude approach or an integration approach. In the amplitude approach, the amplitude of the detector signal is examined directly for the presence of an alternating component correlated to blood flow pulsatility. In the integration approach, an integrator 267 is included in the TPS 250 for integrating the detector signal, for example using a capacitor. The signal may be integrated over fixed time intervals, which may be on the order of 0.10 to 100 ms for example. The magnitude of the integrated signal at the end of the fixed time interval is stored as a data sample point and corresponds to the amount of light received by the detector during the fixed time interval. The pulsatility of the stored data sample points may then be examined to determine a pulsatility metric for use detecting or confirming a patient condition. Alternatively, the signal may be integrated until a predetermined integrated signal magnitude is reached and the time interval required to reach the predetermined magnitude is stored as a sample data point. A pulsatility metric can then be derived from the stored time intervals. When the integration approach is used to obtain detector signal data, the fixed integration time interval or the predetermined integrated signal magnitude are selected to allow the signal sample points to be at or above a sampling frequency needed to ascertain a periodicity of the pulsatile signal that corresponds to an expected range of heart rates. For example, a maximum heart rate may be on the order 240 beats per minute. As such, a desired sampling rate may be approximately 30 to 50 Hz such that about 10 sample points are acquired during each 250 ms cardiac cycle.

The sampling rate may be based on an expected maximum sinus heart rate. At very high heart rates associated with non-sinus tachycardia, the pulsatility signal associated with blood pressure fluctuations within a cardiac cycle will be attenuated. Thus detection of a pulsatile signal based on a sampling rate associated with a maximum sinus rate allows the presence of a sinus rhythm as evidenced by a pulsatile fluctuation in the optical signal to be distinguished from non-sinus tachycardia or fibrillation as evidenced by an absence of or greatly diminished pulsatile fluctuation in the optical signal at designated sampling rate. A rapidly diminishing pulsatile signal indicates impaired blood pressure that may be associated with a life-threatening arrhythmia and need for therapy.

The detector signal data, which may be analog or digitized amplitude signal data and/or integrated signal data, is passed to a processor 268 configured to derive a pulsatility metric from the detector signal. Processor 268 may correspond to microprocessor 54 or dedicated logic or processing circuitry such as tissue perfusion module 72 shown in FIG. 2.

Figure 5:
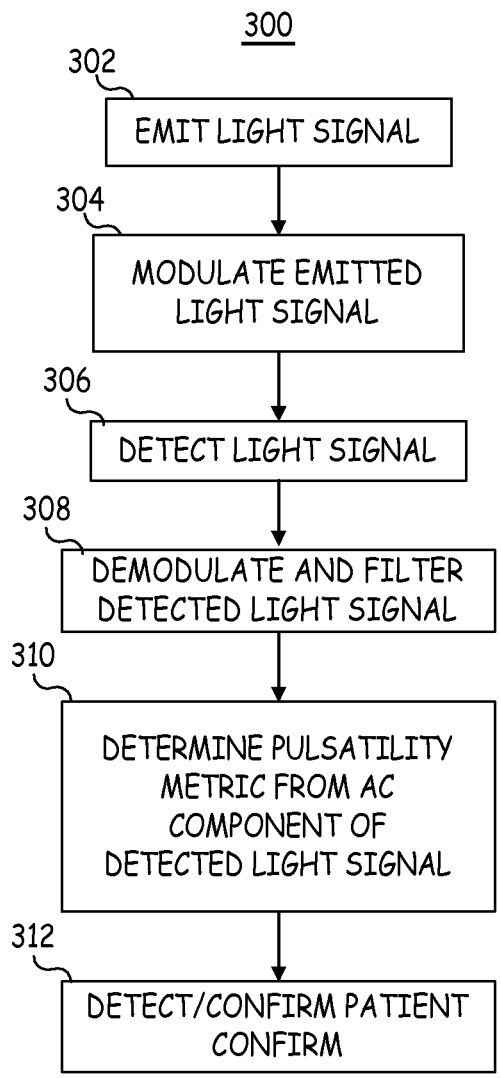
FIG. 5 is a flow chart of a method for monitoring tissue perfusion according to one embodiment of the invention.

FIG. 5 is a flow chart of a method 300 for monitoring tissue perfusion according to one embodiment of the invention. Flow chart 300 and other flow charts presented herein are intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern implantable medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 302, a light signal is emitted from a TPS in response to a driver signal delivered to the light emitting portion of the TPS under the control of timing and control circuitry. The emitted signal may be a narrow-band of light wavelengths or a targeted light wavelength, for example visible red light. As described previously, the emitted light signal may be modulated at block 304 using a carrier frequency of, for example 100 to 10,000 Hz.

At block 306, the emitted light signal, which has been scattered by a volume of body tissue back to the light detecting portion of the TPS, is detected by a light detector. One or more light wavelengths may be detected. The light detector generates a signal responsive to at least one wavelength of the emitted light signal. The detected light signal includes an alternating current component that is correlated to the pulsatility of blood flow through the tissue. At block 308 the light detector signal is processed by integrated circuitry included on the same circuit board as the light detector or by processing circuitry included in an associated implantable medical device. The light detector signal may be demodulated if the emitted signal was modulated using a carrier frequency. The light detector signal may additionally or alternatively be filtered to include frequencies corresponding to an expected patient heart rate range.

The processor determines a pulsatility metric from the alternating current component of the detected light signal at block 310. The metric may be determined based on a peak-to-peak amplitude of the alternating current component and/or a frequency of the alternating current component. At block 312, a patient condition is detected or confirmed using the derived pulsatility metric.

Figure 6:
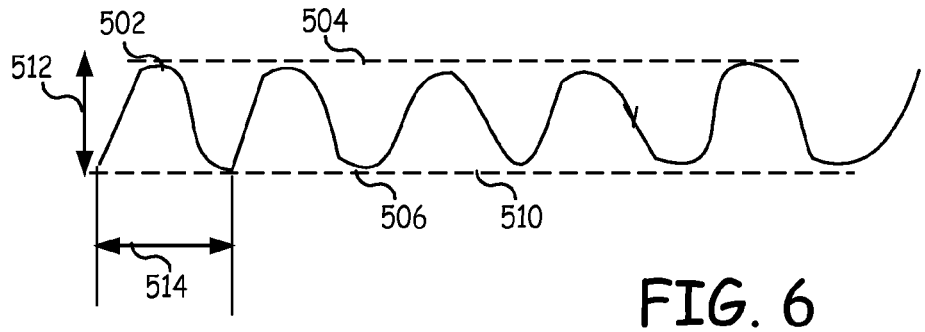
FIG. 6 is an illustration of an alternating current (AC) component of a light detector signal.

FIG. 6 is an illustration of a TPS light detector signal 500 including an alternating current (AC) component corresponding to pulsatility of blood flow through the light-scattering tissue volume. The AC component is characterized by a cyclic variation in the light signal having a periodicity that correlates to the patient's heart rate. The AC component is further characterized by maximum signal peaks 502 alternating with minimum signal peaks 506. A peak-to-peak amplitude 512 of the AC component may be determined as the difference between a maximum peak amplitude 504 and a minimum peak amplitude 510. The maximum peak amplitude 504 and the minimum peak amplitude 510 are determined based on the amplitude of one or more maximum peaks 502 and one or more minimum peaks 506, respectively. The maximum and minimum peak amplitudes 504 and 510 may be computed as an average, median, maximum, minimum or other function of a discreet number of peaks or a moving window of peaks.

The frequency of the AC component of the light detector signal 500 may be computed based on one or more cycle intervals 514. A cycle interval 514 is computed as the time interval between two consecutive peaks, which may be two maximum peaks 502 or two minimum peaks 506. The frequency of the AC component may be used in addition to or alternatively to the peak-to-peak amplitude of the AC component of light detector signal 500 for determining a pulsatility metric for assessing tissue perfusion.

Figure 7:
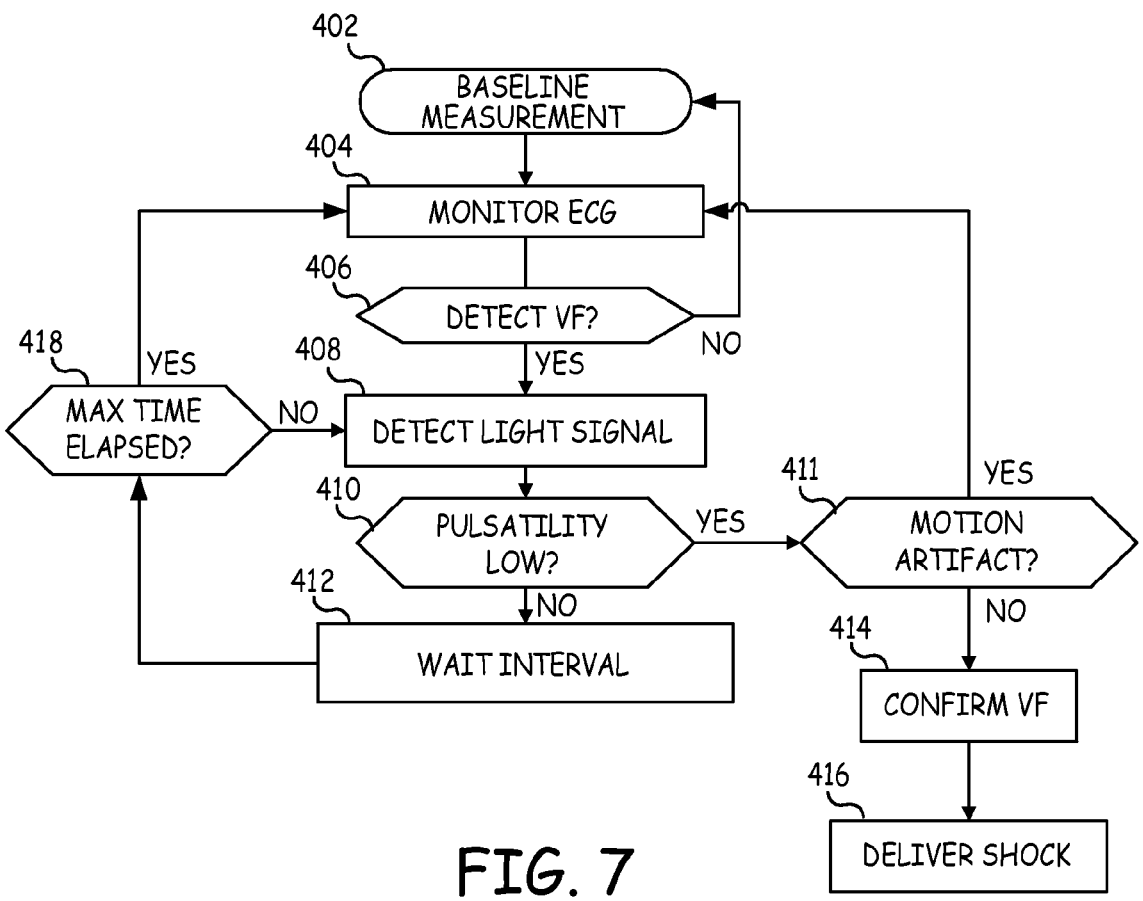
FIG. 7 is a flow chart of a tissue perfusion monitoring method for use in an ICD.

FIG. 7 is a flow chart of a tissue perfusion monitoring method for use in an ICD. Method 400 employs a method of detecting a state of tissue perfusion for confirming a need for delivery of a defibrillation shock. Method 400 may be used, for example, in a SubQ ICD when low amplitude fibrillation signals become more difficult to detect using subcutaneously implanted electrodes. At block 402, a baseline tissue perfusion measurement may be made. A baseline measurement is optional depending on the measurement methods used. A TPS may be pre-calibrated such that baseline comparisons are not needed. Alternatively, a series of measurements may be made during a suspected physiological event to detect a worsening state of tissue perfusion with relative comparisons between sequential measurements being made rather than comparisons to a pre-event baseline measurement.

The perfusion measurements used in method 400 include determining a pulsatility metric from an AC component of a light detector signal. The pulsatility metric may be complimentary to other optical sensing methods for determining a physiological state of the targeted tissue volume.

At block 404, subcutaneous ECG or intracardiac EGM signals are monitored using available sensing electrodes. The cardiac electrical signals are evaluated for detecting cardiac arrhythmias. If an arrhythmia, such as ventricular fibrillation (VF) is detected using cardiac electrical signals, as determined at block 406, tissue perfusion (TP) monitoring is initiated at block 408. An emitted light signal is detected by the TPS at block 408 and used to determine a pulsatility metric. The pulsatility metric is compared to the baseline measurement or a predetermined threshold to determine if tissue perfusion is significantly decreased at block 410. A low level or complete disappearance of the pulsatility of the light detector signal is indicative of insufficient cardiac output and supports the confirmation of an arrhythmia detection at block 414.

Alternatively, the pulsatility metric determined as a frequency of the detector signal AC component is compared to a heart rate determined from the ECG signals at block 414. The frequency of the pulsatile component of the TPS signal may be used to confirm a detected heart rate. A fast heart rate may be confirmed when the frequency of the AC component approximately matches the detected heart rate. If the fast heart rate detected using ECG signal is much higher than the frequency of the TPS signal, the fast heart rate detection may be due to oversensing. On the other hand, a slow heart rate detected using ECG signals may be due to undersensing, which can be verified by comparing the pulsatility frequency of the TPS signal to the ECG detected heart rate.

In some embodiments, the ECG signal sensed at block 404 may be used as a gating signal for controlling monitoring for the pulsatile optical signal at 408 to occur at an expected time delay following cardiac depolarization as detected as a sensed R-wave. Gating the optical signal sensing could reduce the effects of signal noise. Gating the optical signal could further be used to verify detection of a pulse in the optical signal following an appropriately sensed R-wave and detect T-wave oversensing as evidenced by the absence of a pulse signal relative to the oversensed event. Gating the optical signal could further be used to define a normal pulsatile signal morphology that occurs during a known normal sinus rhythm at one or more heart rates. The normal pulsatile signal morphology could be used to distinguish between a normal pulsatile signal and an altered, diminished or absent pulsatile signal during an arrhythmia. Gating of the optical signal to the ECG signal could be controlled by gating light emission by the light source and/or gating light detection by the light detector.

Pulsatility measurements may be repeated at predetermined intervals beginning after the VF detection to determine if a decreasing state of tissue perfusion is occurring. Detection of a decreasing state of tissue perfusion can be used to confirm the VF detection and the need for delivering a therapy. At block 412, method 400 waits a predetermined time interval after making the first measurement, for example 20 to 40 seconds. If a maximum time interval has elapsed, for example 2 to 5 minutes, or a maximum number of pulsatility measurements have been made, as determined at block 418, method 400 returns to block 404 to continue monitoring the ECG/EGM. A decreased state of tissue perfusion is not detected.

If the maximum time interval has not elapsed, another pulsatility measurement is made at block 408 using the detected light signal. The new pulsatility measurement is compared to the previous measurement at block 410 to determine if the pulsatility metric has significantly decreased. If not, method 400 waits another predetermined interval and repeats steps 408 through 412 until a state of decreased pulsatility is detected or until the maximum monitoring time has elapsed. If a state of decreased pulsatility is detected, the arrhythmia detection is confirmed at block 414 and a therapy is delivered at block 416.

In some embodiments, the TPS signal may be examined for motion artifact at block 411, prior to confirming a VF detection based on a low or lack of pulsatility in the TPS signal. Motion artifact will produce large shifts in the baseline TPS signal. The presence of motion artifact may be used as an indicator of patient activity, which would be inconsistent with a VF detection. Large motion artifact would indicate the patient is active and such activity may be interfering with normal ECG and TPS pulsatility sensing. As such, detection of motion artifact signal at block 411 may prevent a confirmation of VF detection. Instead method 400 continues monitoring the ECG signal at block 404. If no motion artifact is present, the VF detection is confirmed at block 414.

Thus, a device and associated methods for monitoring tissue perfusion have been presented in the foregoing description with reference to specific embodiments. It is appreciated that various modifications to the referenced embodiments may be made without departing from the scope of the invention as set forth in the following claims.

The invention claimed is:

1. An implantable medical device for monitoring blood flow pulsatility in a volume of body tissue in a patient, the device comprising:
    at least two electrodes for sensing a cardiac electrical signal;
    a light source for emitting a modulated light signal;
    a filter for filtering the wavelengths of the modulated light signal scattered by the volume of body tissue;
    a light detector for receiving the filtered modulated light signal and emitting a current signal having an alternating current component correlated to pulsatility of blood flow within the volume of body tissue;
    a processor for receiving the cardiac electrical signal, detecting an arrhythmia in response to the cardiac electrical signal, receiving the light detector signal, determining a pulsatility metric in response to the alternating current component of the light detector signal, comparing the pulsatility metric to a heart rate determined from the cardiac electrical signal, confirming the arrhythmia in response to the comparison, and detecting T-wave oversensing in response to the cardiac electrical signal being greater than the pulsatility metric, wherein the pulsatility metric is a frequency of the alternating current component and; and
    a therapy control module coupled to the processor and delivering an anti-arrhythmia therapy in response to the arrhythmia confirmation.

2. The device of claim 1, wherein the processor is further configured to detect T-wave undersensing in response to the pulsatility metric being greater than the cardiac electrical signal.

3. The device of claim 1, wherein the processor confirms the arrhythmia in response to the pulsatility metric being approximately equal to the cardiac electrical signal.

4. The device of claim 1, further comprising a signal modulator modulating the emitted light signal wherein the processor demodulates light detector signal.

5. The device of claim 4 wherein the emitted light signal is modulated at a carrier frequency of approximately 100 to 10,000 Hz.

6. The device of claim 1, wherein the light detector is a photo darlington device.

7. The device of claim 1, wherein the processor determines one of a frequency of the alternating current component and a peak-to-peak amplitude difference of the alternating current component.

8. The device of claim 7 wherein the processor determines a heart rate from the cardiac electrical signals and compares the determined heart rate to the frequency of the alternating current component.

9. The device of claim 1, wherein the processor further determines the presence of a motion artifact in the light detector signal.

\* \* \* \* \*